(12) United States Patent
Dugard

(10) Patent No.: US 10,634,657 B2
(45) Date of Patent: Apr. 28, 2020

(54) PILE TESTING DEVICE

(71) Applicant: Aaron Mark Dugard, Beausejour (CA)

(72) Inventor: Aaron Mark Dugard, Beausejour (CA)

(73) Assignee: 6422277 Manitoba Ltd., Beausejour (CA)

(*) Notice: Subject to any disclaimer, the term of this patent is extended or adjusted under 35 U.S.C. 154(b) by 0 days.

(21) Appl. No.: 16/285,575

(22) Filed: Feb. 26, 2019

(65) Prior Publication Data

US 2019/0324007 A1 Oct. 24, 2019

Related U.S. Application Data

(60) Provisional application No. 62/659,220, filed on Apr. 18, 2018.

(51) Int. Cl.
*G01N 33/00* (2006.01)
*G01N 33/24* (2006.01)
*E02D 5/52* (2006.01)
*E02D 5/56* (2006.01)

(52) U.S. Cl.
CPC ............ *G01N 33/24* (2013.01); *E02D 5/526* (2013.01); *E02D 5/56* (2013.01); *E02D 2600/20* (2013.01)

(58) Field of Classification Search
CPC .......... G01N 33/24; E02D 5/526; E02D 5/56; E02D 2600/20
USPC ........................................................ 73/784
See application file for complete search history.

(56) References Cited

U.S. PATENT DOCUMENTS

| 4,852,719 | A | * | 8/1989 | Lapeyre | B65G 33/12 198/666 |
|---|---|---|---|---|---|
| 5,172,587 | A | | 12/1992 | Long | |
| 5,282,701 | A | | 2/1994 | An et al. | |
| 6,216,803 | B1 | * | 4/2001 | Deken | E21B 15/006 173/188 |
| 10,385,531 | B2 | * | 8/2019 | Suver | E02D 27/50 |
| 2002/0008328 | A1 | * | 1/2002 | Williams | E02D 5/36 264/32 |
| 2006/0198706 | A1 | * | 9/2006 | Neville | E02D 7/22 405/252.1 |
| 2011/0229272 | A1 | * | 9/2011 | Lindsay | E02D 5/56 405/253 |
| 2016/0333540 | A1 | * | 11/2016 | Kaufman | E02D 5/526 |

* cited by examiner

*Primary Examiner* — Max H Noori
(74) *Attorney, Agent, or Firm* — Ryan W. Dupuis; Ade & Company Inc.; Kyle R. Satterthwaite

(57) ABSTRACT

A pile testing device for testing ground includes (i) a tubular outer pile member having a helical flight mounted externally thereon, (ii) an inner pile member received within the second pile, (iii) a coupling assembly operable between an inserting position in which the inner pile member and the outer pile member are joined in fixed relation to one another so as to be arranged to be simultaneously driven into the ground and a testing position in which the inner pile member is longitudinally slidable relative to the outer pile member within a prescribed axial range but in which the inner pile member remains coupled to rotate together with the outer pile member, (iv) a jack coupled between top ends of the inner and outer pile members, and (v) a sensor adapted to measure longitudinal displacement of one of the pile members relative to the other pile member or the ground.

20 Claims, 6 Drawing Sheets

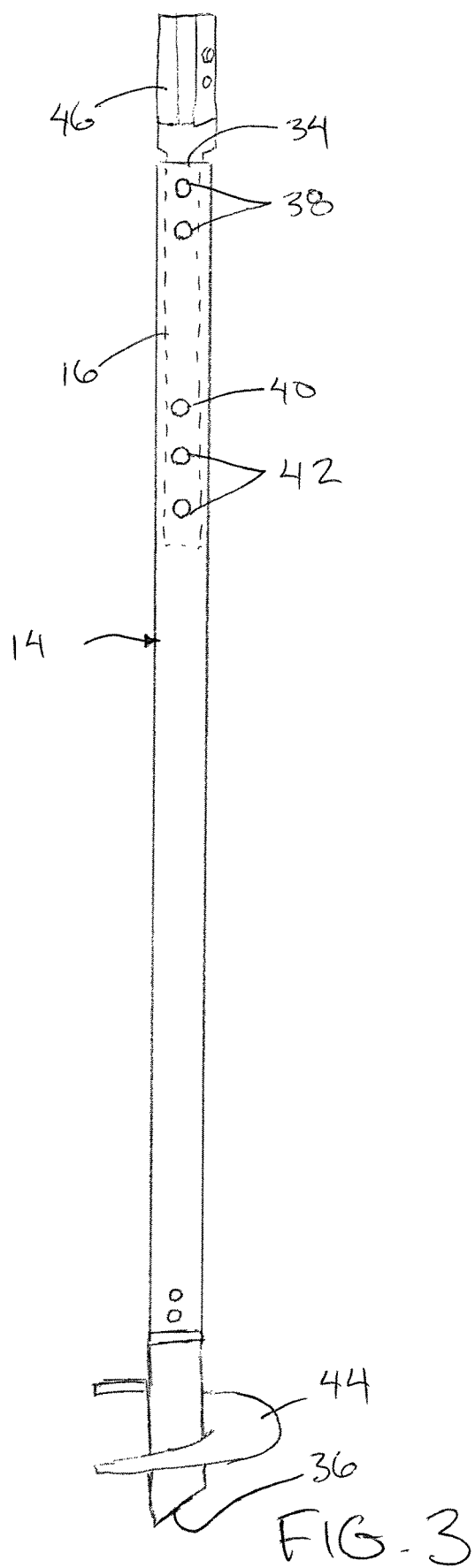
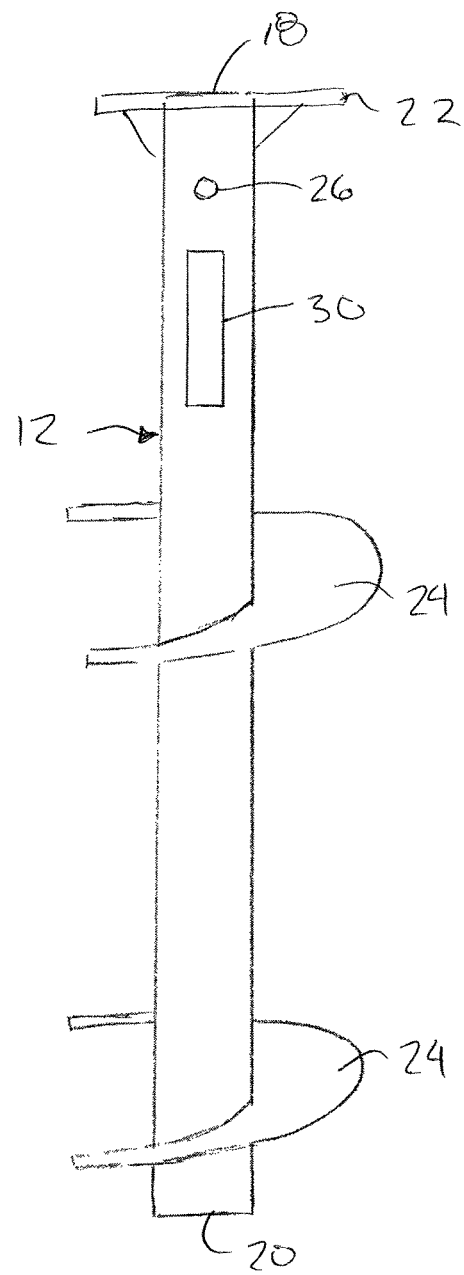
FIG. 3
FIG. 4

PILE TESTING DEVICE

This application claims the benefit under 35 U.S.C.119(e) of U.S. provisional application Ser. No. 62/659,220, filed Apr. 18, 2018.

FIELD OF THE INVENTION

The present invention relates to a pile testing device for testing ground conditions in relation to a pile. The present invention further relates to features of a helical member on a pile.

BACKGROUND

In the manufacture of various structures, the use of piles penetrated into the ground below the structure is well known for stabilizing the structure relative to the ground. The number of piles to be used, the configuration of the piles, and the placement of the piles relative to one another will vary depending upon the condition of the ground and the type of structure. To better gauge the condition of the ground, it is well known to use a test pile penetrated into the ground which is loaded with longitudinally applied force while the subsequent displacement of the pile relative to the ground is monitored.

In an attempt to provide reliable testing results in an efficient manner, various devices have been proposed, for example as described in U.S. Pat. Nos. 5,172,587 by Long and 5,282,701 by Samsung Construction Co., Ltd. The devices proposed are limited in their ability to represent a variety of different screw pile configurations in an efficient manner which allows for rapid deployment and recovery of the testing device.

SUMMARY OF THE INVENTION

According to one aspect of the invention there is provided a pile testing device for testing ground, the pile testing device comprising:

an outer pile member comprising a tube which is elongate in a longitudinal direction between opposing top and bottom ends of the outer pile member and a helical flight mounted externally on the tube;

an inner pile member comprising a shaft which is received within the second pile to extend longitudinally outwardly beyond the top and bottom ends of the outer pile member;

a coupling assembly operable between an inserting position in which the inner pile member and the outer pile member are joined in fixed relation to one another so as to be arranged to be simultaneously driven into the ground and a testing position in which the inner pile member is longitudinally slidable relative to the outer pile member within a prescribed axial range and the inner pile member is coupled to rotate together with the outer pile member;

a jack adapted to be coupled between the top end of the outer pile member and a top end of the inner pile member so as to apply a longitudinal force to the pile members acting to longitudinal displace one of the pile members relative to the other pile member in the testing position of the coupling assembly; and a sensor adapted to measure longitudinal displacement of at least one of the pile members relative to either one of the other pile member or the ground.

The configuration of the coupling assembly allows for rapid deployment of the testing device by penetrating the inner and outer pile members of the device simultaneously into the ground, followed by simultaneously removing the inner and outer pile members from the ground upon completion of the testing procedure.

Optionally, the inner pile member may further comprise a helical flight mounted on the shaft below the bottom end of the outer pile member. Preferably the helical flight on the inner pile member and the helical flight on the outer pile member lie along a common helical path about a longitudinal axis of the inner pile member.

The coupling assembly preferably includes a first coupling which defines the prescribed axial range of movement of the inner pile member relative to the outer pile member in the testing position and a second coupling which fixes the inner pile member to the outer pile member in the inserting position, in which the second coupling member is releasable independently of the first coupling.

The first coupling may comprise a transverse guide fastener mounted on one of the pile members and a guide slot in the other pile member receiving the guide fastener for longitudinal sliding therein in which the guide slot defines the prescribed axial range in the testing position.

The second coupling may comprise a transverse lock fastener mounted through co-operating apertures in both the inner pile member and the outer pile member to fix the inner pile member relative to the outer pile member.

When the inner pile member is a hollow tube, the coupling assembly may further comprise an inner shaft which is receivable within the inner pile member and which includes fastener apertures therein for fastened connection to one or both of the pile members. Preferably, the inner shaft includes a motor coupling formed at a top end thereof for connection to a drive motor to drive the pile members simultaneously into the ground. Preferably, the inner shaft is directly fastened to both the inner pile member and the outer pile member.

The fastener apertures may include a drive fastener aperture formed in the inner pile member at a location spaced above the outer pile member and receiving a drive fastener therein which directly couples the inner shaft to the inner pile member in the inserting position.

The testing device may further include a helical bolt flange fixed onto the inner pile member and a helical flight mounted onto the inner pile member by fastened connection to the helical bolt flange, and/or a helical bolt flange fixed onto the outer pile member such that the helical flight of the outer pile member is mounted onto the outer pile member by fastened connection to the helical bolt flange.

One of the pile members may further comprise a plurality of modular sections, in which adjacent ones of the modular sections are joined to one another by a helical flange fixed onto the end of each section such that the helical flanges are abutted with one another and fasteners which fasten the helical flanges together.

According to another important independent aspect of the present invention there is provided a pile member comprising:

an elongate shaft;

a helical bolt flange supported on the elongate shaft having a plurality of fastener apertures therein; and a plurality of helical flights having different diameters which are greater than a diameter of the helical bolt flange;

the helical flights each having fastener apertures therein for alignment with corresponding fastener apertures in the helical bolt flange such that the helical flights can be interchangeably mounted onto the helical bolt flange.

According to another important independent aspect of the present invention there is provided pile member comprising:

an elongate shaft formed in a plurality of modular sections;

a helical bolt flange fixed onto an end of each modular section such that the helical bolt flanges of adjacent modular sections are abutted with one another;

a plurality of fasteners which fasten the helical flanges together such that the modular sections are readily releasable from one another by removal of the fasteners.

According to another important independent aspect of the present invention there is provided a method of testing a ground response to a pile, the method comprising providing a pile assembly comprising an outer pile member comprising a tube which is elongate in a longitudinal direction between opposing top and bottom ends of the outer pile member and a helical flight mounted externally on the tube and an inner pile member comprising a shaft which is received within the second pile to extend longitudinally outwardly beyond the top and bottom ends of the outer pile member;

connecting the inner pile member and the outer pile member in fixed relation to one another using a first coupling;

driving rotation of the inner and outer pile members together to drive the inner and outer pile members simultaneously into the ground;

releasing the first coupling and connecting the inner and outer pile members by a second coupling in which the inner pile member is longitudinally slidable relative to the outer pile member within a prescribed axial range while being coupled to rotate together;

applying a longitudinal force to the pile members acting to longitudinal displace one of the pile members relative to the other pile member;

measuring longitudinal displacement of at least one of the pile members relative to either one of the other pile member or the ground; and driving rotation of the inner and outer pile members together to drive the inner and outer pile members simultaneously out of the ground while being connected by the second coupling.

BRIEF DESCRIPTION OF THE DRAWINGS

Some embodiments of the invention will now be described in conjunction with the accompanying drawings in which:

FIG. 3 is an elevational view of the inner pile member and the inner shaft received therein;

FIG. 4 is an elevational view of the outer pile member;

In the drawings like characters of reference indicate corresponding parts in the different figures.

DETAILED DESCRIPTION

Figure 1:
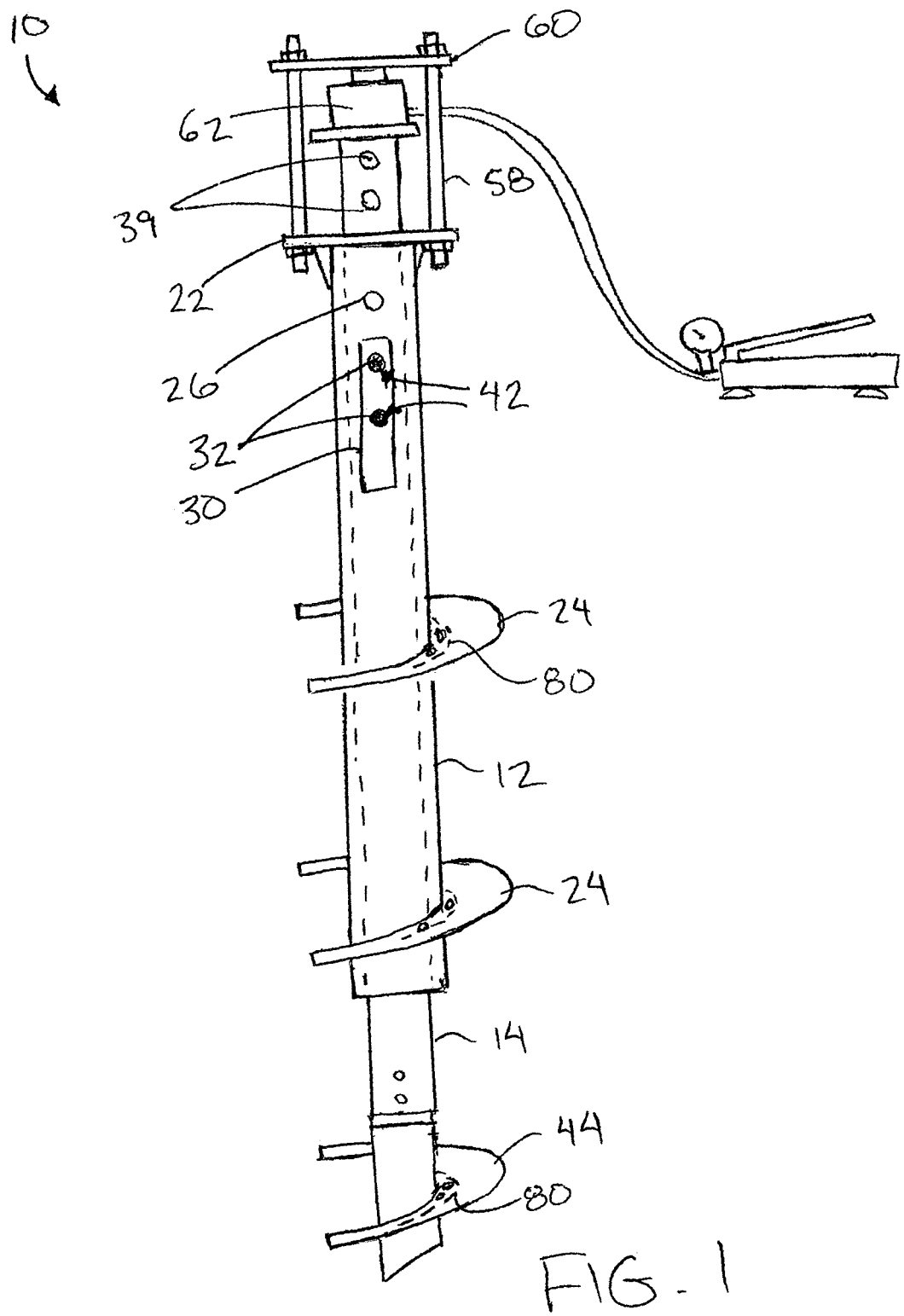
FIG. 1 is an elevational view of the pile testing device in a testing configuration.
Figure 2:
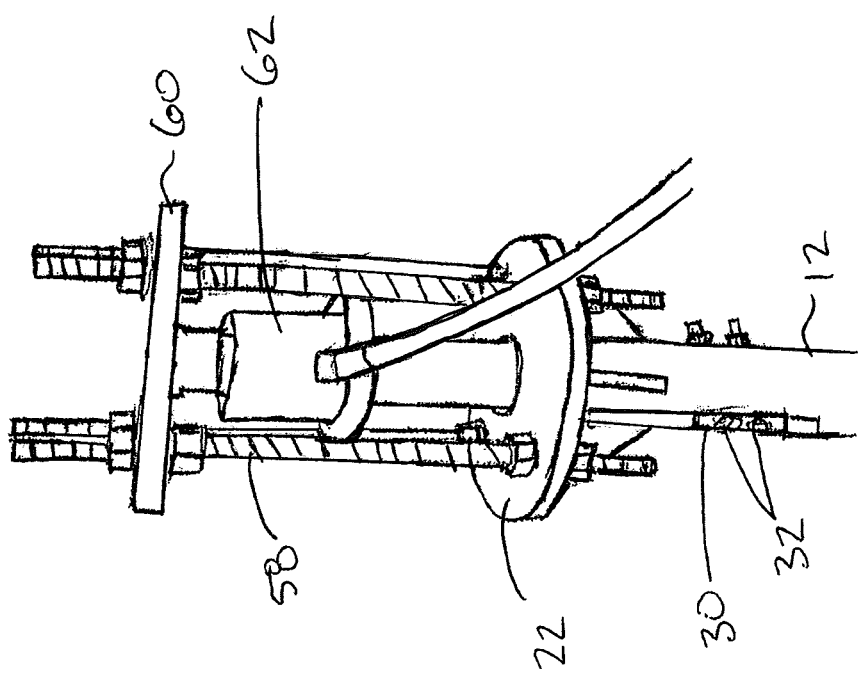
FIG. 2 is a perspective view of a jack coupled between the inner pile member and the outer pile member in the testing configuration.
Figure 5:
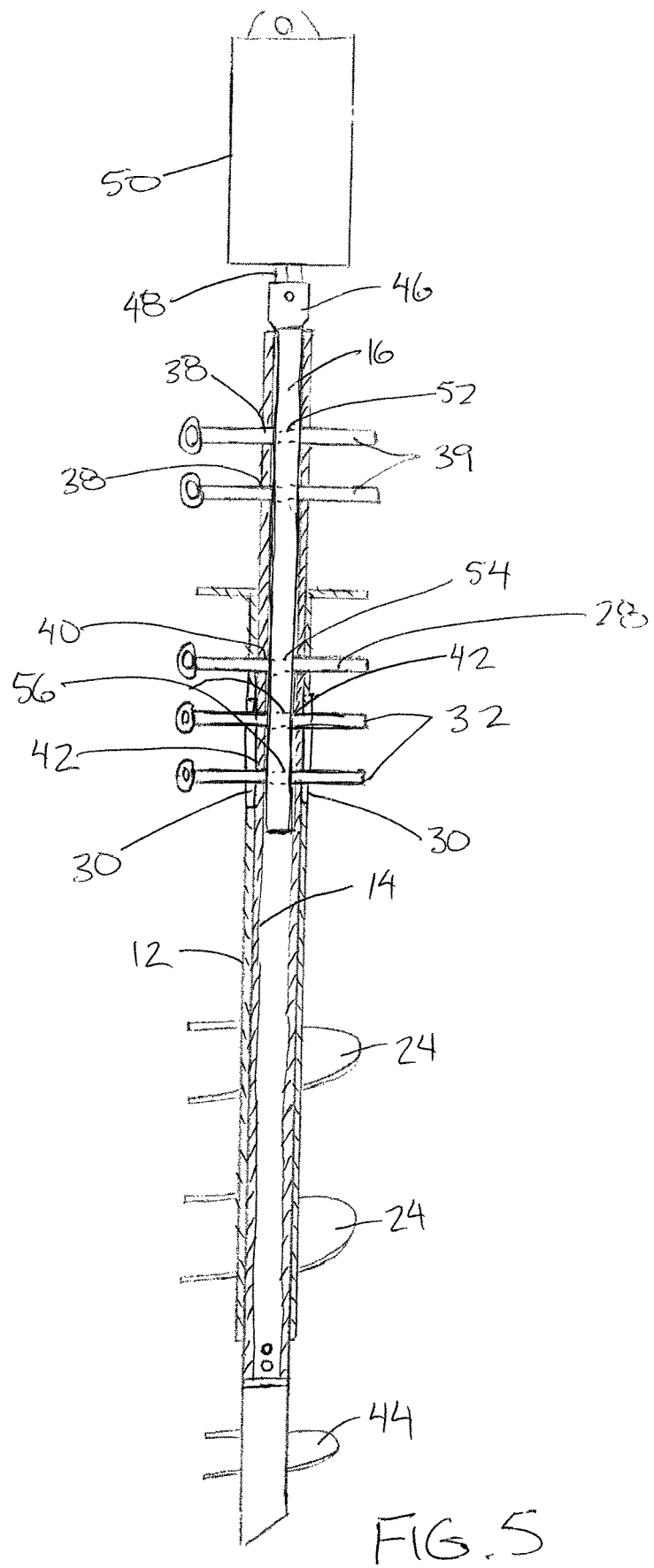
FIG. 5 is a partly sectional view of the pile testing device in the inserting position according to the first embodiment of FIGS. 1 through 4.

Referring to the accompanying figures there is illustrated a pile testing device generally indicated by reference numeral 10. The device 10 is particularly suited for testing ground conditions in relation to a pile, for example by testing the axial movement of a pile relative to the ground in response to an applied force.

The device 10 includes an outer pile member 12, an inner pile member 14 receivable through the outer pile member, and an inner shaft 16 receivable through the inner pile member and which is used for coupling the inner pile member to the outer pile member in a variety of configurations for inserting the pile members into the ground, performing a test, and withdrawing the pile members from the ground as described in further detail below.

The outer pile member 12 comprises a hollow tube which is elongate in a longitudinal direction from an open top end 18 to an open bottom end 20. A circular mounting flange 22 is fixed at the top end of the outer pile member to extend generally radially outward therefrom by being oriented perpendicular to the longitudinal axis of the pile member.

One or more helical flights 24 are mounted externally on the outer pile member 12 in which the helical flights 24 are aligned with one another along a common a helical path so as to be similar in pitch and orientation relative to one another. In the illustrated embodiment, one helical flight 24 is located adjacent the bottom end of the outer pile member, and another helical flight 24 is located centrally along the length at an intermediate location on the outer pile member.

The outer pile member includes a lock aperture 26 extending diametrically through the outer pile member so as to form a pair of holes extending through the wall of the outer pile member at diametrically opposing locations. The lock aperture 26 is suitably arranged for receiving a lock fastener 28 fully through the outer pile member to connect the outer pile member to the inner pile member and/or the inner shaft as described in further detail below.

The outer pile member also includes two guide slots 30 formed therein at diametrically opposing locations on the pile member such that each slot is linear and elongate in the axial direction of the pile member. The two slots are directly opposite one another and are positioned to be closer in proximity to the top end than the bottom end of the outer pile member but at a location spaced below the lock aperture 26. The guide slots 30 cooperate with guide fasteners 32 as described in further detail below.

The inner pile member 14 is an elongate hollow shaft which is generally tubular in shape so as to be elongate in the longitudinal direction of the outer pile member. The hollow passage through the inner pile member extends between the open top end 34 and the open bottom end 36 of the inner pile member. The inner pile member has an outer diameter which is suitable to be received within the inner diameter of the outer pile member such that the inner pile member is longitudinally slidable relative to the outer pile member. The inner pile member is longer than the outer pile member so as to protrude longitudinally outward below the bottom of the outer pile member while simultaneously protruding upward above the top end of the outer pile member.

The inner pile member includes two drive apertures 38 formed therein at longitudinally spaced positions in proximity to the top end of the pile member. Each aperture extends fully through the pile member to define a pair of holes at diametrically opposing locations in the wall of the inner pile member. The drive apertures 38 are aligned with one another within a common longitudinal plane so as to be located spaced one above the other. The drive apertures 38 cooperate with drive fasteners 39 which are used for coupling the inner pile member to the inner shaft 16 as described in further detail below.

The inner pile member also includes a lock aperture 40 which is spaced below the drive apertures 38 so as to be suitable for alignment with the lock aperture 26 of the outer pile member when the two drive apertures are located spaced above the top end of the outer pile member. The inner pile member also includes two guide apertures 42 at longitudinally spaced apart positions below the lock aperture 40. Again each of the apertures comprises a pair of holes which are diametrically aligned with one another in an opposing walls of the inner pile member. The two guide apertures and the lock aperture are all aligned within a common longitudinal plane containing the two drive apertures. In this manner, when the lock aperture 40 is aligned with the lock aperture 26 of the outer pile member, the guide apertures 42 are in alignment with the guide slots 30, typically offset towards one end of the guide slots such that the inner pile member can be longitudinally displaced relative to the outer pile member within a prescribed range while maintaining both guide apertures 42 in alignment with the guide slots.

In the illustrated embodiment, the bottom end of the inner pile member also supports a helical flight 44 thereon. In this instance, when the lock apertures 26 and 40 are aligned, the helical flight 44 of the inner pile member is aligned along a common helical path with the helical flight 24 of the outer pile member so as to be similar in pitch and similar in orientation for following the same path through the ground when driving the inner and outer piles into the ground together.

The inner shaft 16 as an elongate shaft having an outer diameter which is suitably sized for being received within the inner diameter of the inner pile member 14. The inner shaft 16 can be slidably inserted through the open top end of the inner pile member and is arranged to span an overall length between top and bottom ends of the inner shaft member which spans from the top end of the inner pile member to a bottom end of the inner shaft located spaced slightly below the guide apertures 42 respectively.

A suitable coupling 46 is provided in fixed relation to the inner shaft at the top end of the inner shaft which is enlarged relative to the diameter of the inner shaft therebelow. The coupling 46 defines an internal socket therein open to the top end which is suitable for forming a mating connection with the output shaft 48 of a suitable drive motor 50. For example the socket may have a hexagonal cross-section for mating non-rotatably with a shaft having a hexagonal cross-section as well.

The inner shaft 16 is provided with a pair of drive apertures 52 formed therein of suitable size and shape for alignment with the two drive apertures 38 within the inner pile member such that insertion of the drive fasteners 39 within the drive apertures will effectively lock the longitudinal position and prevent relative rotation between the inner shaft 16 and the inner pile member 14. In this manner, rotational drive is transferred directly from the inner shaft to the inner pile member when driving the inner pile member into the ground.

The inner shaft 16 is also provided with a lock aperture 54 for alignment with the lock aperture 40 in the inner pile member when the drive apertures are aligned. In this manner, insertion of a lock fastener 28 through the aligned lock apertures couples the inner shaft 16 relative to both the inner pile member 14 and the outer pile member 12 in a manner which fixes the pile members relative to one another in the longitudinal direction and against relative rotation.

The inner shaft 16 also includes a pair of guide apertures 56 which are aligned with the guide apertures 42 in the inner pile member when the lock aperture 40 is aligned with the lock aperture 54. In this manner, when the guide fasteners 32 are inserted into the guide apertures 42 of the inner pile member and the corresponding guide apertures 56 of the inner shaft 16, the guide fasteners serve to fix the inner shaft relative to the inner pile member. When the guide fasteners comprise bolts, the heads of the guide fasteners and corresponding nuts threaded onto the opposing threaded end of each guide fastener results in the heads and the nuts of the guide fasteners being received within the guide slots of the outer pile member to allow relative longitudinal sliding movement between the inner and outer pile members within the prescribed range defined by the length of the guide slots while restricting relative rotation therebetween, in the absence of any other fastening. When the guide fasteners are transverse pins protruding outwardly through the slots, they provide a similar resistance to relative rotation while enabling longitudinal relative sliding within the prescribed range defined by the slots.

The inner shaft 16, the guide fasteners 32, the lock fastener 28, and the drive fasteners 39 collectively form a coupling assembly which is used for coupling the inner and outer pile members relative to one another in various configurations for inserting the pile members into the ground, performing a test with the pile members, and/or subsequently removing the pile members from the ground as described in the following.

In operation, for initially driving the pile members into the ground, the inner pile member is inserted into the outer pile member, and the inner shaft is inserted into the inner pile member with the lock apertures all being aligned with one another to receive the lock fastener therein. The remaining drive fasteners and guide fasteners are also secured within their respective apertures. The guide fasteners define a first coupling between the inner and outer pile members which serves only to resist relative rotation between the pile members but does not provide an axial support when the guide fasteners are at an intermediate location along the guide slots. The lock fastener defines a second coupling which fully fixes the inner pile member and the outer pile member relative to one another in addition to fixing the outer pile member directly to the inner shaft to transfer torque from the drive motor directly to the outer shaft to assist in driving insertion of the pile members into the ground. The use of drive fasteners between the inner shaft and the inner pile member provides an auxiliary coupling for direct connection of the drive to the inner shaft, however this connection may not be required if suitable resistance to shear forces is provided by the remaining fasteners during the insertion of the pile members into the ground in an inserting position of the coupling assembly.

Once the motor is coupled to the coupling 46 at the top end of the inner shaft 16, the two pile members can be driven into the ground by rotating the pile members simultaneously. The aligned helical flights cooperate together to simultaneously penetrate the pile members into the ground. Once fully penetrated to a suitable depth in which the guide slots are in close proximity to the surface of the ground with the mounting flange 22 of the outer pile member being spaced above the ground surface, the drive motor can be detached from the inner shaft, and the inner shaft can be removed from the inner and outer pile members by removal of all fasteners. Before testing, the guide fasteners are replaced such that the inner and outer pile members are only connected by the guide fasteners 32 in the testing position of the device 10.

A set of circumferentially spaced apart bolts 58 are coupled between the mounting flange 22 and an upper plate 60 mounted parallel and spaced above the mounting flange 22 so as to enable a suitable jack 62 to be mounted between the top end of the inner pile member and the upper plate 60. Expanding the jack 62 acts to push the inner pile member downwardly while pushing the outer pile upwardly. By sizing the helical flights 24 to have more resistance against longitudinal displacement within the ground than the helical flight 44 of the inner pile member 14, the outer pile member is typically resisted from a longitudinal displacement relative to the ground so that it is primarily the inner pile member which is displaced downwardly into the ground during a test.

Suitable sensors are provided for measuring the force applied to the pile members in the longitudinal direction to cause displacement of the pile members relative to one another and relative to the ground. This may be accomplished by inserting a load cell between the jack 62 and either one of the upper plate 60 or the inner pile member. Alternatively, if using a hydraulic jack, a pressure sensor can be used to monitor the hydraulic pressure of the jack from which the longitudinal force applied to the pile member can be calculated.

Sensors are also provided for monitoring the longitudinal displacement of the pile members relative to one another and/or relative to the ground. Linear displacement sensors may be coupled between the pile members for measuring relative displacement. Alternatively, the flow of hydraulic fluid can be measured to determine displacement of the hydraulic jack for translating the displacement into a linear measurement. In a further arrangement, the sensors may measure relative displacement between the pile members and/or relative to a suitable reference structure mounted separately on the ground.

Once suitable data has been collected it is possible to calculate a load rating for a pile configured similarly to the inner pile member of the pile testing device.

Upon completion of the test, both inner and outer pile members are removed from the ground using the inner shaft 16 and the drive motor 50. Subsequent to removal of the guide fasteners, the inner shaft 16 is again inserted into the open top end of the inner pile member 14 such that the drive apertures 38 and 52 are aligned with one another so that the drive fasteners can be re-attached. In this position, the guide apertures 42 will be aligned with the guide apertures 56 which in turn should be aligned with the guide slots to permit the guide fasteners to be reinserted. This corresponds to the removing position of the coupling assembly. Coupling the motor to the coupling 46 of the top end of the inner shaft and operating the drive motor in reverse will simultaneously transfer drive rotation to both the inner and outer pile members to withdraw the pile members from the ground by action of the helical flights 24 and 44.

As shown in FIG. 1, each of the helical flights may be mounted onto the respective pile member using a bolt flange 80 which follows the helical path of the helical flights and which is mounted in fixed relation on the exterior of the pile member. Each helical flight is larger in diameter than the bolt flange and mounts directly adjacent the bolt flange along the length of the bolt flange to permit a series of bolts to be fastened through the helical flight and the bolt flange which in turn fixes the helical flight relative to the pile member. In this manner, a plurality of different helical flights may be provided which differ in diameter from one another but which include a similar pattern of bolt apertures formed therein such that the different size helical flights can be interchangeably mounted onto the respective bolt flanges of the pile members. The test device can thus be varied in configuration for testing the ground response to different pile member configurations.

Figure 6:
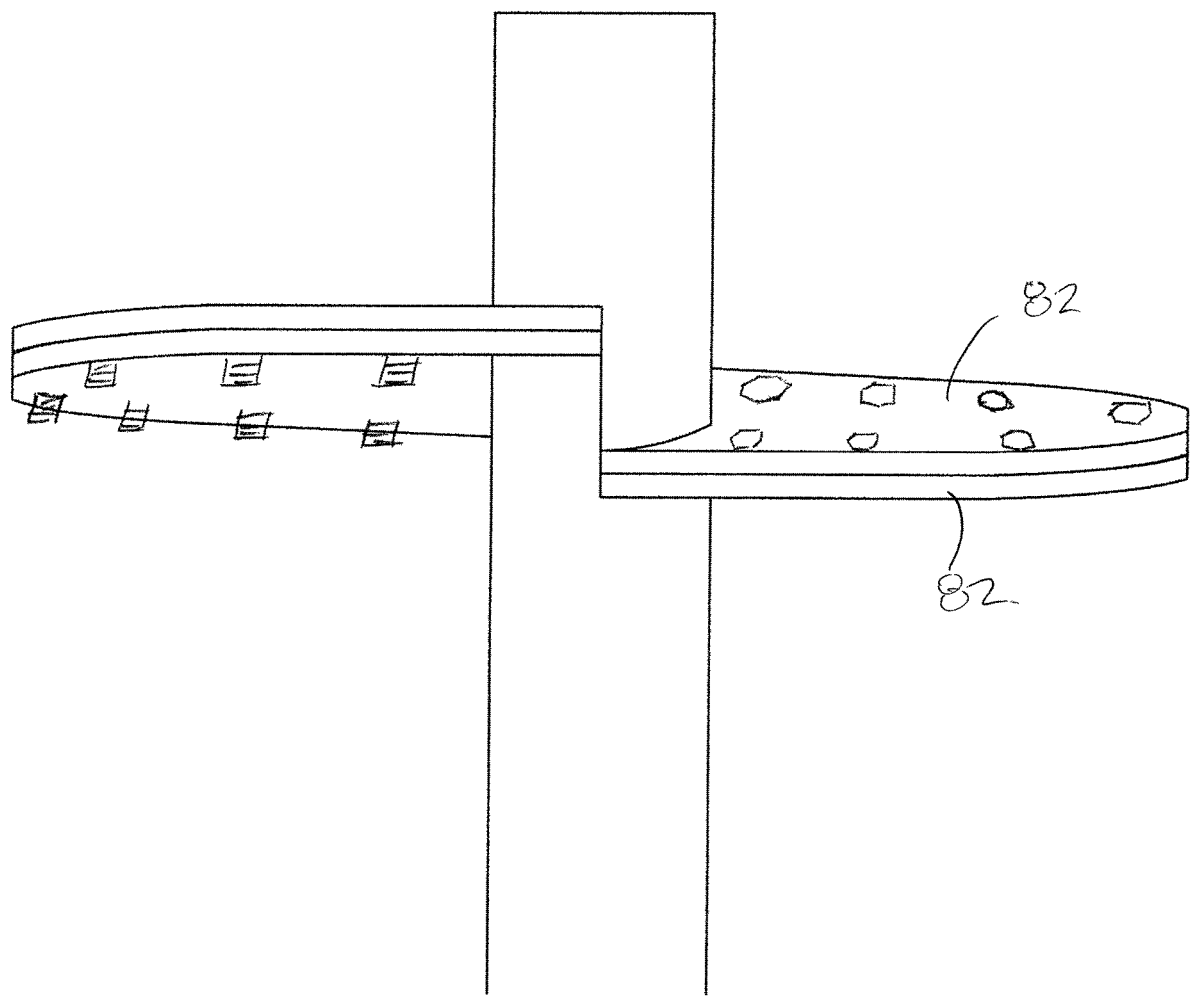
FIG. 6 is an elevational view of an alternative embodiment of one of the pile members in which the pile member is formed in modular sections abutted in series with one another.

As shown in FIG. 6, one or both of the pile members may be formed in a plurality of modular sections which are abutted in series with one another in the longitudinal direction. The abutted ends of two adjacent pipe sections are each formed such that the edge at the end of the tubular wall forming the pile member is cut along the same helical path as the helical flights. More particularly the edge at the end of each modular section follows the helical path of 360° about the pile with the opposing ends being joined by a remaining linear edge extending in the axial direction. When both ends of the adjacent modular sections are similarly formed, the two sections can be abutted end to end to form a continuous tubular peripheral wall of the pile member with the linear edges being abutted as shown in FIG. 6. Each end of the abutted modular sections is also provided with a helical bolt flange 82 which follows the helical path 360° about the pile member at the end of the modular section. In this manner, the helical bolt flanges 82 of two abutted ends lie directly adjacent one another about the full circumference of the pile member. A plurality of threaded fasteners coupled between the abutted helical bolt flanges serves to maintain the modular sections coupled in fixed relation to one another. Removal of the fasteners permits one of the modular sections to be separated from the pile member for varying the overall length of the pile member as desired. As shown in FIG. 6, the fasteners each extends through both helical bolt flanges in an axial direction of the shaft, at spaced apart positions from one another in a circumferential direction about the shaft.

Figure 7:
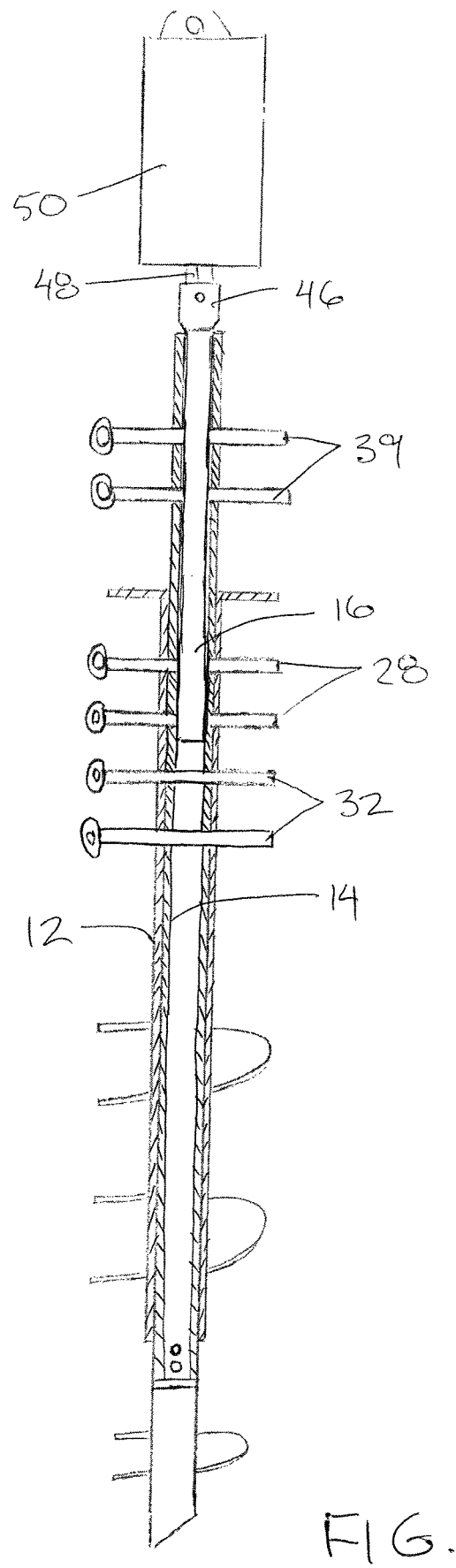
FIG. 7 is a partly sectional view of the pile testing device according to a further embodiment.

In an alternative configuration as shown in FIG. 7, the inner shaft may have a length which spans from the top of the inner pile member across the location of the lock aperture, however the inner shaft does not overlap the location of the guide apertures and the guide slot in the pile members. In this instance, the lock aperture preferably comprises two or more lock apertures which are longitudinally spaced. In this instance, in the inserting position, drive fasteners in the drive apertures at the top of the inner pile member and lock fasteners received within the lock apertures of the inner and outer pile members are sufficient to directly transmit drive from the motor to both pile members. The guide fasteners can remain mounted within the inner pile member for alignment with the guide slots and the outer pile member, however these are not relied on for transferring drive during insertion of the piles into the ground. Once inserted into the ground, both the drive fasteners and lock fasteners can be removed so that the guide fasteners remain the only connection between the inner and outer pile members in the testing position. Testing is accomplished in the same manner as the previous embodiments. When the pile members are to be removed from the ground, the inner shaft in this instance is only coupled to the inner pile member using the drive fasteners at a location spaced above the outer pile member so that the motor directly drives the inner pile member, however the transfer of rotational drive from the inner pile member to the outer pile member relies only upon interaction of the guide fasteners in the inner pile member with the guide slots in the outer pile member to simultaneously drive rotation of both pile members during removal of the pile members from the ground.

In further embodiments, the connection of the jack to the pile members may be reconfigured such that the jack instead exerts a downward pushing force on the outer pile member, simultaneously with an upward pulling force on the inner pile member.

The structures described herein with regard to an inner pile received within an outer pile, as well as the use of helical flanges for joining adjacent modular sections can be used in the construction of a composite screw pile. In this instance, the assembled composite pile member may include an upper section having a shaft with a first prescribed diameter, and a lower section with a shaft having a second prescribed diameter which is less than the first prescribed diameter. The upper and lower sections of the pile member may be coupled by helical bolt flanges at the ends of the pipe sections which are joined in the manner according to FIG. 6, or alternatively, the inner shaft may be received within a hollow interior of the outer pile member with the use of transverse fasteners coupling the pile members in fixed relation to one another.

Since various modifications can be made in my invention as herein above described, and many apparently widely different embodiments of same made, it is intended that all matter contained in the accompanying specification shall be interpreted as illustrative only and not in a limiting sense.

The invention claimed is:

1. A pile testing device for testing ground, the pile testing device comprising:
    an outer pile member comprising a tube which is elongate in a longitudinal direction between opposing top and bottom ends of the outer pile member and a helical flight mounted externally on the tube;
    an inner pile member comprising a shaft which is received within the outer pile member to extend longitudinally outwardly beyond the top and bottom ends of the outer pile member;
    a coupling assembly operable between an inserting position in which the inner pile member and the outer pile member are joined in fixed relation to one another so as to be arranged to be simultaneously driven into the ground and a testing position in which the inner pile member is longitudinally slidable relative to the outer pile member within a prescribed axial range and the inner pile member is coupled to rotate together with the outer pile member;
    a jack adapted to be coupled between the top end of the outer pile member and a top end of the inner pile member so as to apply a longitudinal force to the pile members acting to longitudinally displace one of the pile members relative to the other pile member in the testing position of the coupling assembly; and
    a sensor adapted to measure longitudinal displacement of at least one of the pile members relative to either one of the other pile member or the ground.

2. The device according to claim 1 wherein the inner pile member further comprises a helical flight mounted on the shaft below the bottom end of the outer pile member.

3. The device according to claim 2 wherein the helical flight on the inner pile member and the helical flight on the outer pile member lie along a common helical path about a longitudinal axis of the inner pile member.

4. The device according to claim 1 wherein the coupling assembly includes a first coupling which defines the prescribed axial range of movement of the inner pile member relative to the outer pile member in the testing position and a second coupling which fixes the inner pile member to the outer pile member in the inserting position, the second coupling member being releasable independently of the first coupling.

5. The device according to claim 4 wherein the first coupling comprises a transverse guide fastener mounted on one of the pile members and a guide slot in the other pile member receiving the guide fastener for longitudinal sliding therein in which the guide slot defines the prescribed axial range in the testing position.

6. The device according to claim 4 wherein the second coupling comprises a transverse lock fastener mounted through co-operating apertures in both the inner pile member and the outer pile member to fix the inner pile member relative to the outer pile member.

7. The device according to claim 1 wherein the inner pile member is a hollow tube and wherein the coupling assembly further comprises an inner shaft which is receivable within the inner pile member and which includes fastener apertures therein for fastened connection to one or both of the pile members, the inner shaft including a motor coupling formed at a top end thereof for connection to a drive motor to drive the pile members simultaneously into the ground.

8. The device according to claim 7 wherein the inner shaft is directly fastened to both the inner pile member and the outer pile member.

9. The device according to claim 7 wherein the fastener apertures include a drive fastener aperture formed in the inner pile member at a location spaced above the outer pile member and receiving a drive fastener therein which directly couples the inner shaft to the inner pile member in the inserting position.

10. The device according to claim 1 further comprising a helical bolt flange fixed onto the inner pile member and a helical flight mounted onto the inner pile member by fastened connection to the helical bolt flange.

11. The device according to claim 1 further comprising a helical bolt flange fixed onto the outer pile member, the helical flight of the outer pile member being mounted onto the outer pile member by fastened connection to the helical bolt flange.

12. The device according to claim 1 wherein one of the pile members comprises a plurality of modular sections, adjacent ones of the modular sections being joined to one another by a helical flange fixed onto the end of each section such that the helical flanges are abutted with one another and fasteners which fasten the helical flanges together.

13. A pile member comprising:
    an elongate shaft formed in a plurality of modular sections;
    a helical bolt flange fixed onto an end of each modular section such that the helical bolt flanges of an adjacent pair of the modular sections are abutted with one another;
    a plurality of fasteners coupled between the helical flanges of said adjacent pair of the modular sections such that the modular sections of said adjacent pair of the modular sections are coupled together so as to be readily releasable from one another by removal of the fasteners.

14. A method of using the pile testing device according to claim 1 for testing a ground response to a pile, the method comprising
    connecting the inner pile member and the outer pile member in fixed relation to one another using the inserting position of the coupling assembly;
    driving rotation of the inner and outer pile members together to drive the inner and outer pile members simultaneously into the ground;
    releasing the inserting position of the coupling assembly and connecting the inner and outer pile members using the testing position of the coupling assembly in which the inner pile member is longitudinally slidable relative to the outer pile member within a prescribed axial range while being coupled to rotate together;

applying a longitudinal force to the pile members acting to longitudinal displace one of the pile members relative to the other pile member;

measuring longitudinal displacement of at least one of the pile members relative to either one of the other pile member or the ground; and driving rotation of the inner and outer pile members together to drive the inner and outer pile members simultaneously out of the ground while being connected using the testing position of the coupling assembly.

15. The pile member according to claim 13 wherein the modular sections of said adjacent pair of the modular sections are coupled together solely by the fasteners coupled between the helical flanges of the modular sections.

16. The pile member according to claim 13 wherein the helical flanges of said adjacent pair of the modular sections lie directly adjacent one another as they extend in a circumferential direction about the shaft.

17. The pile member according to claim 13 wherein the helical flanges of said adjacent pair of the modular sections abut one another about a full circumference of the pile member.

18. The pile member according to claim 13 wherein the modular sections of said adjacent pair of the modular sections of the shaft each include a linear edge extending in an axial direction of the shaft at the end of the modular section that supports the helical flange thereon, and wherein the linear edges abut one another when the two modular sections are abutted end to end with one another.

19. The pile member according to claim 13 wherein the modular sections of said adjacent pair of the modular sections of the shaft each include an end edge at the end of the modular section that supports the helical flange thereon in which the end edge and the helical flange follow a common helical path, and wherein the end edges of said adjacent pair of modular sections abut one another when the two modular sections are abutted end to end with one another.

20. The pile member according to claim 13 wherein the fasteners each extend through both of the helical flanges of said adjacent pair of the modular sections in an axial direction of the elongate shaft such that the fasteners are spaced apart from one another in a circumferential direction about the shaft.

* * * * *